United States Patent
Kakee

(10) Patent No.: US 8,382,669 B2
(45) Date of Patent: Feb. 26, 2013

(54) ULTRASONIC DIAGNOSTIC APPARATUS AND ULTRASONIC DIAGNOSTIC APPARATUS CONTROL METHOD

(75) Inventor: Akihiro Kakee, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1270 days.

(21) Appl. No.: 12/062,100

(22) Filed: Apr. 3, 2008

(65) Prior Publication Data

US 2008/0249405 A1 Oct. 9, 2008

(30) Foreign Application Priority Data

Apr. 5, 2007 (JP) ................................ 2007-099246

(51) Int. Cl.
*A61B 8/14* (2006.01)
(52) U.S. Cl. ......... 600/437; 600/439; 600/440; 600/443
(58) Field of Classification Search .................. 600/437, 600/439, 440, 443
See application file for complete search history.

(56) References Cited

U.S. PATENT DOCUMENTS

| 6,398,733 | B1 | 6/2002 | Simopoulos et al. | |
| 7,481,768 | B2 * | 1/2009 | Sasaki | 600/443 |
| 2002/0172374 | A1 * | 11/2002 | Bizjak | 381/71.14 |
| 2003/0236459 | A1 * | 12/2003 | Loftman et al. | 600/437 |
| 2006/0116578 | A1 * | 6/2006 | Grunwald et al. | 600/440 |
| 2007/0164817 | A1 * | 7/2007 | Randall et al. | 330/107 |
| 2008/0249405 | A1 * | 10/2008 | Kakee | 600/437 |

FOREIGN PATENT DOCUMENTS

| JP | 2648771 | 5/1997 |
| JP | 2004-500915 | 1/2004 |
| WO | WO 01/80714 A2 | 11/2001 |

* cited by examiner

*Primary Examiner* — Tse Chen
*Assistant Examiner* — Baisakhi Roy
(74) *Attorney, Agent, or Firm* — Oblon, Spivak, McClelland, Maier & Neustadt, L.L.P.

(57) ABSTRACT

A living tissue region determining unit of a gain correction data generating section determines a diagnostic living tissue region on the basis of an S/N and a dispersion value of ultrasound data collected from each of a plurality of slice sections in a gain correction scan mode intended for the generation of gain correction data for volume data. A gain correction map generating unit applies a least squares method to the average value of the ultrasound data in a plurality of regions set by dividing the living tissue region into predetermined sizes, thereby generating two-dimensional gain correction maps. Then, an interpolating processing unit interpolates, in a slice direction, the gain correction map generated for each of the plurality of slice sections, and generates three-dimensional gain correction data corresponding to each voxel of the volume data.

17 Claims, 8 Drawing Sheets

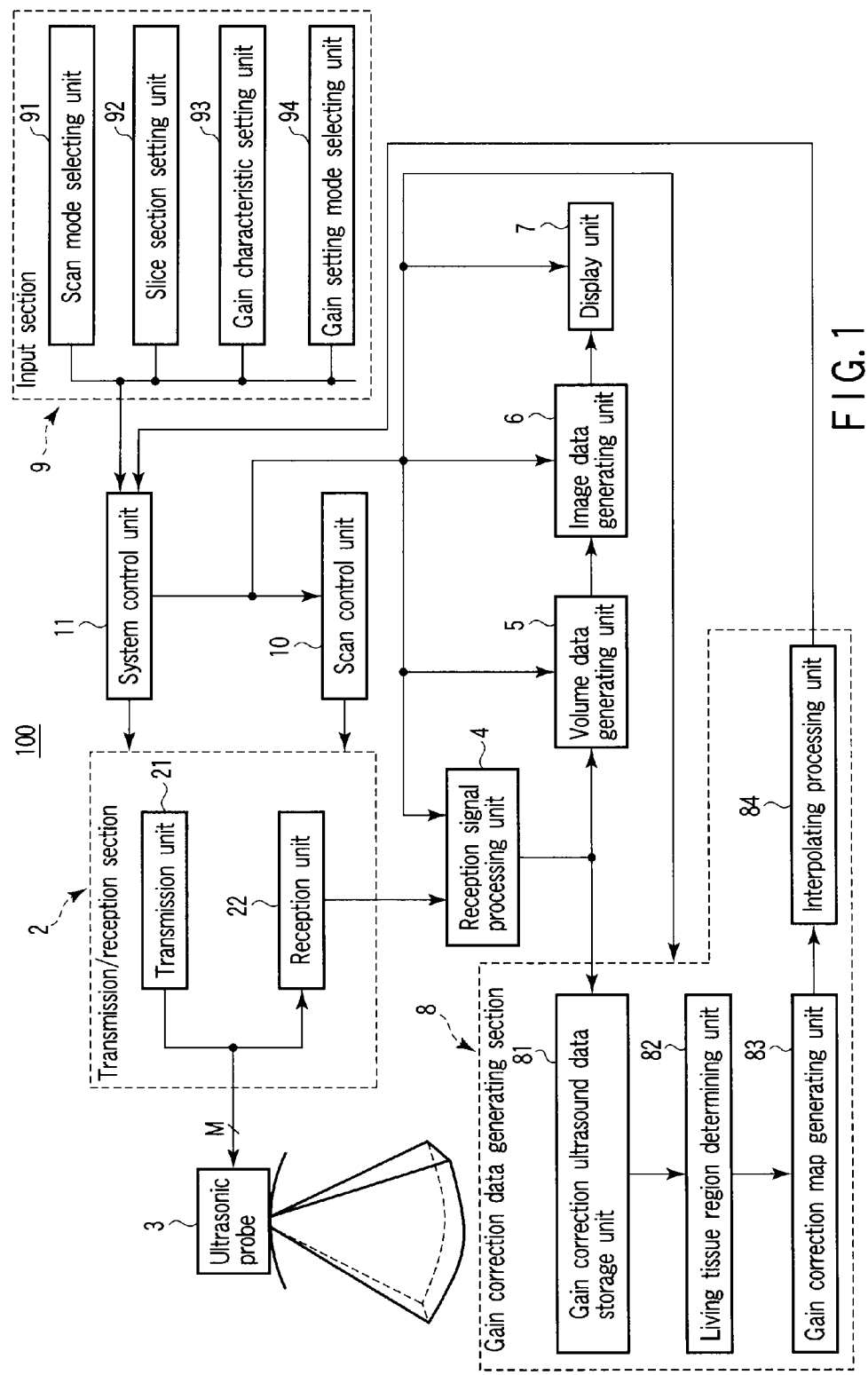
F I G. 1

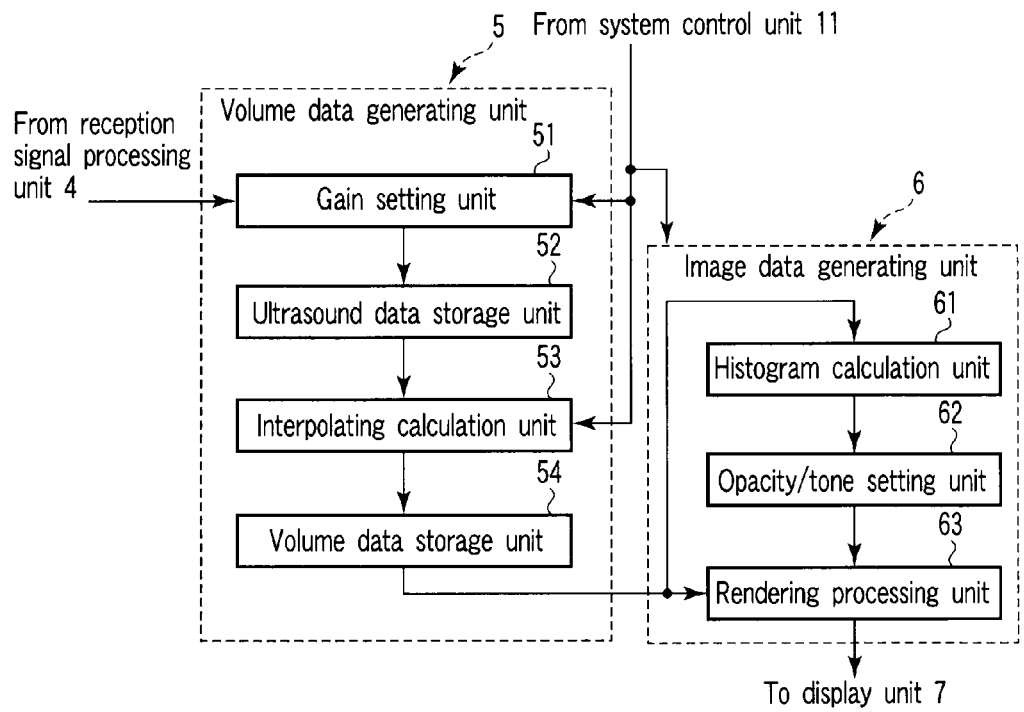
F I G. 4
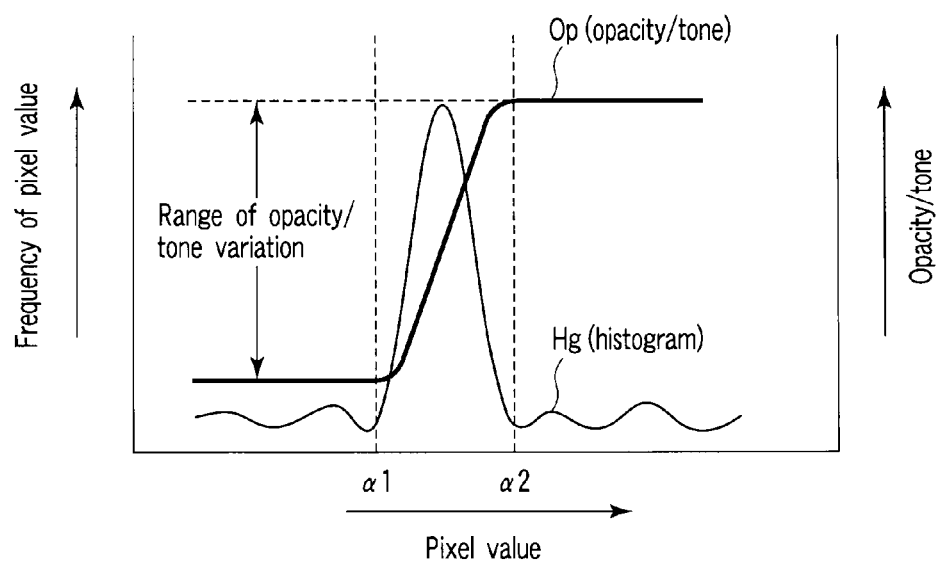
F I G. 5

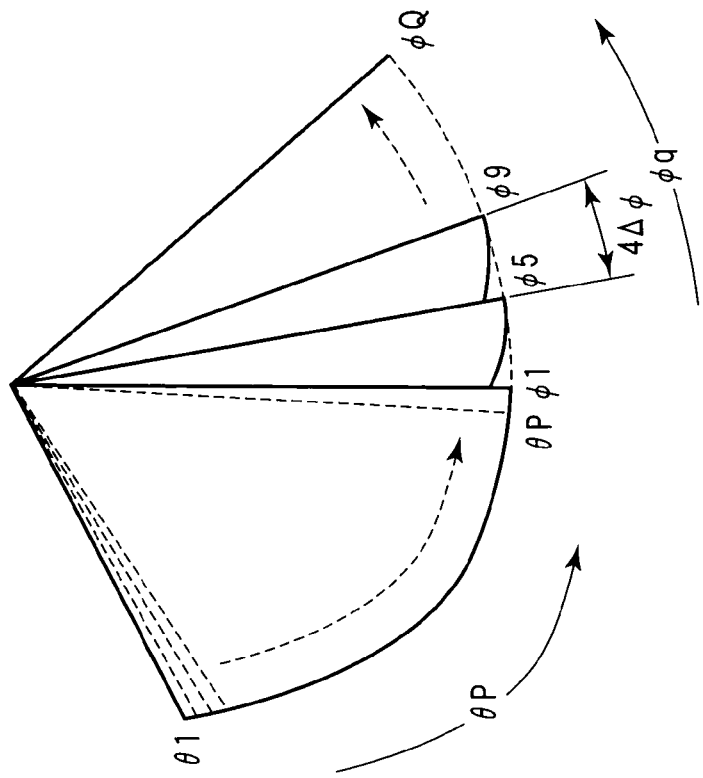
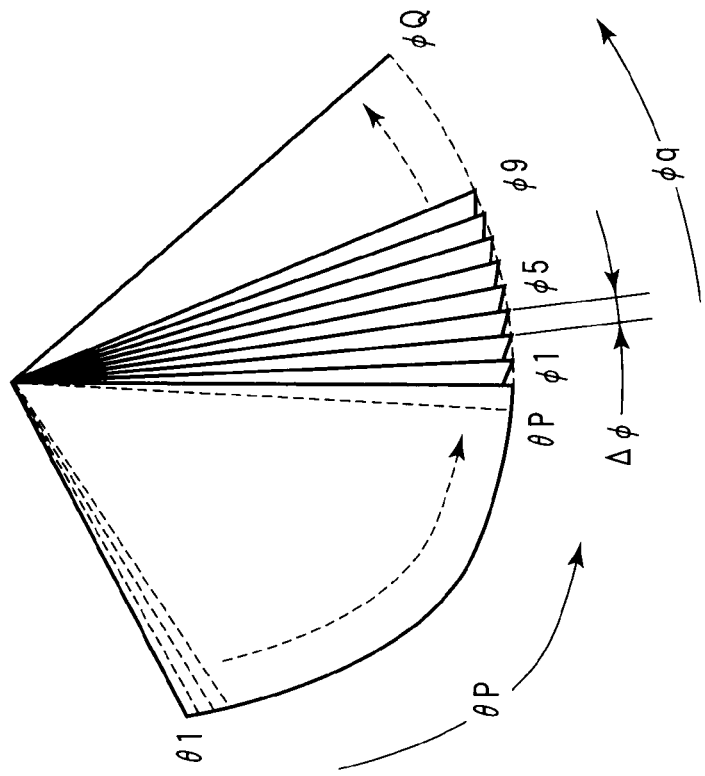

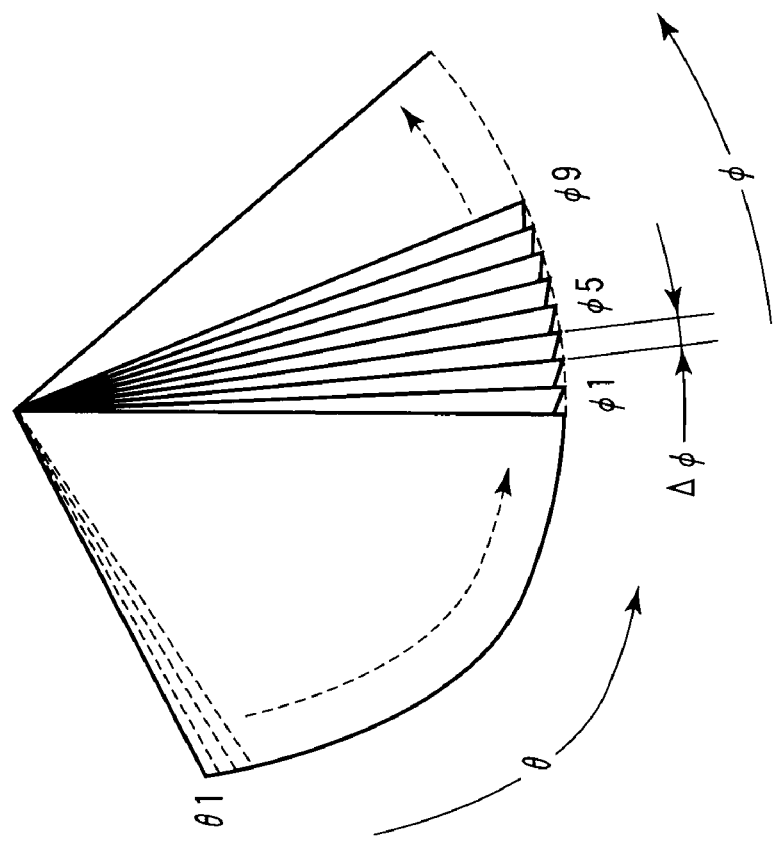
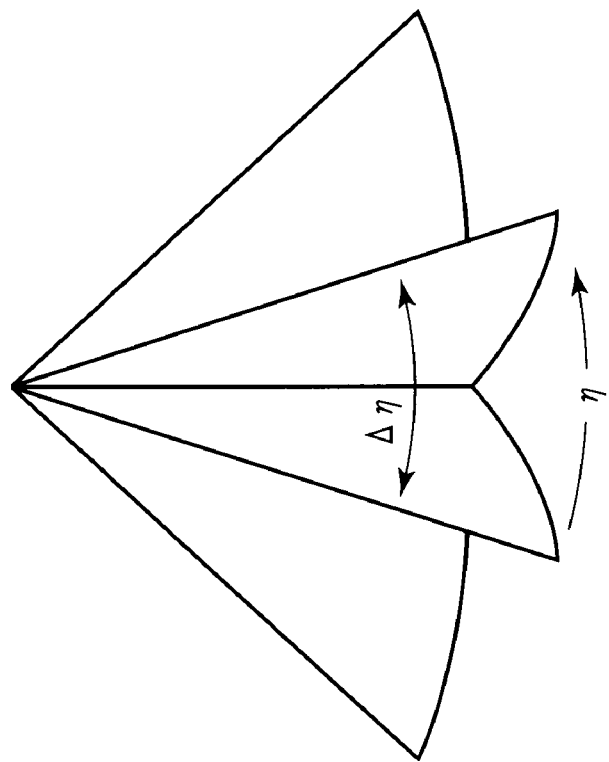
FIG. 9A
FIG. 9B

ULTRASONIC DIAGNOSTIC APPARATUS AND ULTRASONIC DIAGNOSTIC APPARATUS CONTROL METHOD

CROSS-REFERENCE TO RELATED APPLICATIONS

This application is based upon and claims the benefit of priority from prior Japanese Patent Application No. 2007-099246, filed Apr. 5, 2007, the entire contents of which are incorporated herein by reference.

BACKGROUND OF THE INVENTION

1. Field of the Invention

The present invention relates to an ultrasonic diagnostic apparatus, and more particularly, it relates to an ultrasonic diagnostic apparatus and an ultrasonic diagnostic apparatus control method capable of automatically setting a gain for a reception signal collected from a specimen.

2. Description of the Related Art

An ultrasonic diagnostic apparatus transmits and receives ultrasonic waves in a plurality of directions of a specimen using an ultrasonic probe in which a plurality of oscillating elements are arranged, and displays, on a monitor, image data generated on the basis of reflected waves obtained at the time. This apparatus enables a real-time observation of two-dimensional image data or three-dimensional image data on the inside of a body by a simple operation of touching the ultrasonic probe with the body surface, and is therefore widely used to diagnose the shapes or functions of various organs.

Such an ultrasonic diagnostic apparatus generally comprises an ultrasonic probe having oscillating elements for transmitting/receiving ultrasonic waves to/from a specimen, a sending unit for supplying a drive signal to the oscillating elements, a receiving unit for performing processing such as a gain correction for a reception signal obtained from the oscillating element, an image data generating unit for generating image data on the basis of the processed reception signal, and a display unit for displaying the generated image data.

The reception sensitivity in the transmission/reception of the ultrasonic waves carried out by the ultrasonic diagnostic apparatus having the above-mentioned basic configuration is dependent on the shape and tissue characterization of an organ which propagates the ultrasonic waves at this moment and further dependent on, for example, the degree of obesity of the specimen. Therefore, when the two-dimensional image data for the specimen is to be collected and displayed, an operator operates a gain correcting function provided in an input section under the observation of the image data displayed in real time on the display unit of the apparatus, thereby correcting the gain for the reception signal and generating image data having a preferred sensitivity distribution.

However, this method requires a new gain correction every change in the position or direction of a slice section (scan section) of the image data for a diagnostic part of the specimen, so that inspection efficiency significantly decreases, which has been a major problem particularly when ultrasound tests are conducted in a short time for a large number of specimens as in a screening test in, for example, a medical checkup.

In order to improve such a problem, there has been proposed a method of automatically correcting the gain of a reception signal on the basis of previously collected information on the amplitude of this reception signal (e.g., refer to Patent document 1 and Patent document 2.).

To automatically correct the gain of a reception signal, Patent Publication No. 2648771 describes a method comprising detecting a peak position of a histogram generated on the basis of information on the amplitude of this reception signal, and setting a gain correction value on the basis of the difference between the peak position of the histogram and a preset reference value corresponding to the average luminance of image data.

Furthermore, PCT National Publication No. 2004-500915 describes a method comprising determining a diagnostic living tissue region on the basis of the S/N of two-dimensional ultrasound data obtained from slice sections and a specimen or the dispersion value of a histogram, and setting a two-dimensional gain correction map for correcting a local gain or a dynamic range in the living tissue region on the basis of the amplitude information and noise level concerning the ultrasound data in the living tissue region.

Recently, attention has been focused on a method comprising transmitting/receiving ultrasonic waves to/from a three-dimensional region of a specimen, and generating three-dimensional image data or two-dimensional image data in an arbitrary section on the basis of volume data collected at the time. Methods of collecting the volume data in practical use include a method which moves or turns an ultrasonic probe having a plurality of one-dimensionally arranged oscillating elements in a direction perpendicular to the arrangement direction, and a method using an ultrasonic probe having a plurality of two-dimensionally arranged oscillating elements (two-dimensional array ultrasonic probe).

The above-mentioned volume data is usually generated by composing ultrasound data obtained in a plurality of sequential slice sections. Then, when such volume data is subjected to a gain correction in accordance with, for example, the method described in Patent document 1 or Patent document 2, it is necessary to set the above-mentioned gain correction values or gain correction maps for the two-dimensional ultrasound data obtained from a large number of slice sections and further set three-dimensional gain correction data on the basis of the obtained gain correction values or gain correction maps, which requires a storage circuit having a high capacity to store the ultrasound data for use in the gain correction and also requires much time spent on setting the three-dimensional gain correction data. It has therefore been difficult to display, in real time or in a short time, for example, three-dimensional image data based on the volume data which has subjected to the gain correction by the application of the above-mentioned methods.

BRIEF SUMMARY OF THE INVENTION

The present invention has been made in view of such a conventional problem, and it is an object of the present invention to provide an ultrasonic diagnostic apparatus and an ultrasonic diagnostic apparatus control method capable of automatically correcting, in a short time, for example, the gain of volume data for a specimen relative to a voxel value in collecting the volume data.

According to an aspect of the present invention, there is provided an ultrasonic diagnostic apparatus which generates volume data on the basis of ultrasound data collected by transmitting/receiving ultrasonic waves to/from a three-dimensional region of a specimen, and displays, in real time, image data obtained by processing the volume data, the apparatus comprising: a gain correction data generating section which generates three-dimensional gain correction data for the volume data on the basis of the ultrasound data; and a gain setting unit which sets, on the basis of the gain correction data, the gain of at least one of a reception signal obtained from the specimen by the transmission/reception of the ultrasonic waves and the ultrasound data generated by processing the reception signal.

According to another aspect of the present invention, there is provided a method of controlling an ultrasonic diagnostic apparatus which generates volume data on the basis of ultrasound data collected by transmitting/receiving ultrasonic waves to/from a three-dimensional region of a specimen, and displays, in real time, image data obtained by processing the volume data, the method comprising: generating three-dimensional gain correction data for the volume data on the basis of the ultrasound data; and setting, on the basis of the gain correction data, the gain of at least one of a reception signal obtained from the specimen by the transmission/reception of the ultrasonic waves and the ultrasound data generated by processing the reception signal.

BRIEF DESCRIPTION OF THE SEVERAL VIEWS OF THE DRAWING

FIG. 1 is a block diagram showing the whole configuration of an ultrasonic diagnostic apparatus in an embodiment of the present invention;

FIG. 4 is a block diagram showing the configurations of a volume data generating unit and an image data generating unit provided in the ultrasonic diagnostic apparatus in the present embodiment;

FIG. 5 is a diagram for explaining a histogram of volume data in the present embodiment and the opacity/tone set in accordance with this histogram;

FIG. 6A and FIG. 6B are diagrams showing three-dimensional ultrasound data collected in a volume data collection scan mode of the present embodiment, and ultrasound data for a plurality of slice sections collected in a gain correction scan mode;

FIG. 9A and FIG. 9B are diagrams showing slice sections in the gain correction scan mode in a modification of the present embodiment.

DETAILED DESCRIPTION OF THE INVENTION

Figure 2:
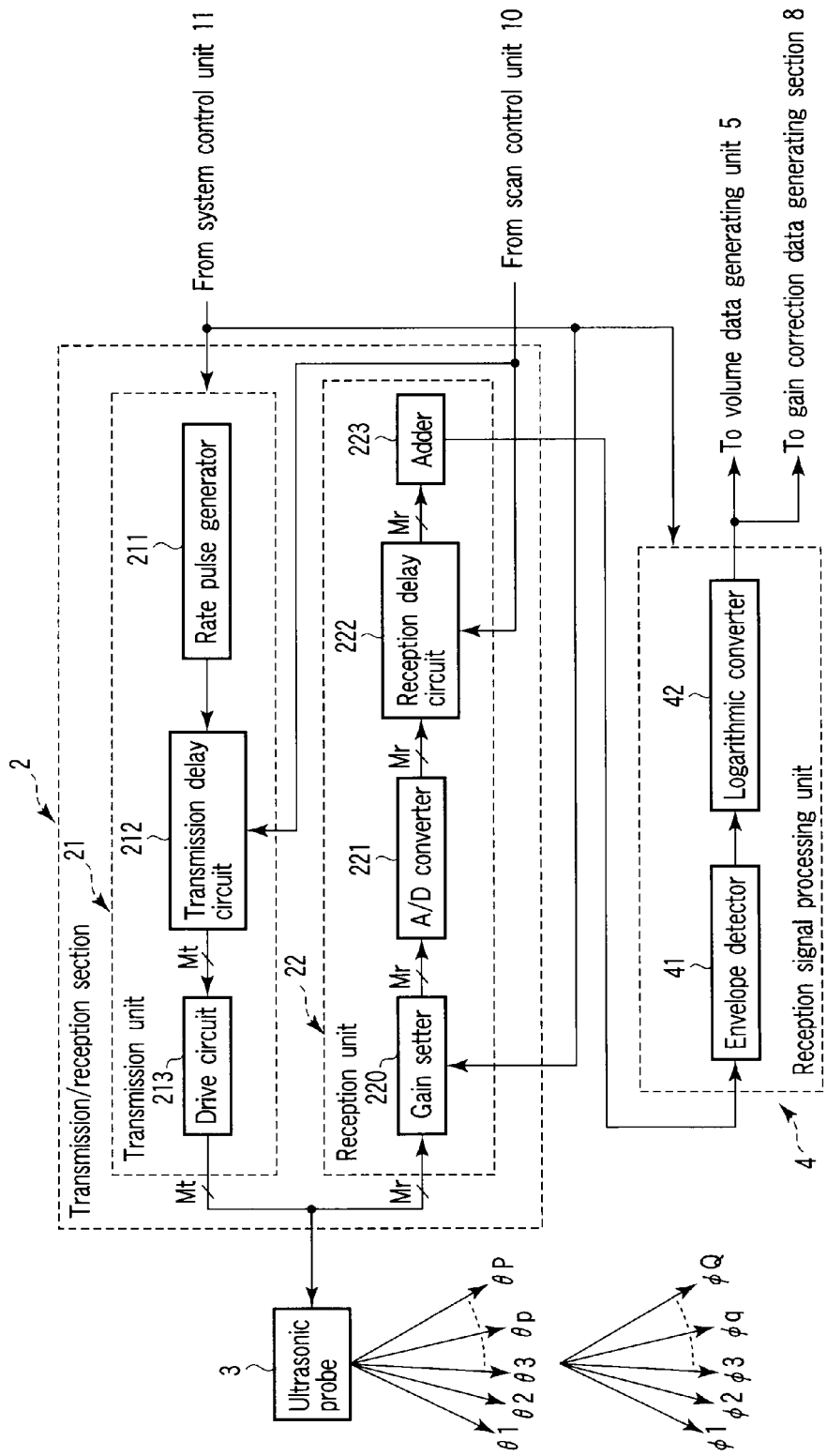
FIG. 2 is a block diagram showing the specific configurations of a transmission/reception section and a reception signal processing unit provided in the ultrasonic diagnostic apparatus in the present embodiment.

Hereinafter, an embodiment of the present invention will be described with reference to the drawing. It is to be noted that about the same signs are assigned to components having the same function and configuration in the following description and that a repetitive explanation is only given when necessary.

In the embodiment of the present invention described below, a first normal ultrasound data (biological data) in a plurality of predetermined slice sections and second ultrasound data (noise data) obtained without any transmission/reception of ultrasonic waves are collected in a gain correction scan mode intended for the generation of gain correction data for volume data collected from a specimen of interest, such that a diagnostic living tissue region is determined on the basis of the S/N of obtained from the difference between the biological data and the noise data and on the basis of the dispersion value of the biological data in each of a plurality of first regions set by dividing the slice section into predetermined sizes.

Then, the plurality of adjacent first regions are bundled into predetermined sizes to form second regions, and a least squares method is applied to the average value of the biological data in each of the plurality of second regions, thereby generating a two-dimensional gain correction map. Further, the gain correction map in each of the plurality of slice sections set for a three-dimensional region of the specimen is interpolated in a slice direction to generate three-dimensional gain correction data corresponding to each voxel of the volume data.

In addition, in the case of the embodiment described below, a gain correction is made to volume data collected by an ultrasonic probe having two-dimensionally arranged oscillating elements. However, the present invention is not limited to this, and, for example, a gain correction may be made to volume data obtained by mechanically moving or turning an ultrasonic probe having a plurality of one-dimensionally arranged oscillating elements. Moreover, volume data is generated on the basis of B mode data obtained by transmitting/receiving ultrasonic waves to/from a three-dimensional region in the case described below, but volume data may be generated on the basis of other ultrasound data such as color Doppler data.

(Configuration of the Apparatus)

The configuration of an ultrasonic diagnostic apparatus in the embodiment of the present invention is described with FIG. 1 to FIG. 6. In addition, FIG. 1 is a block diagram showing the whole configuration of the ultrasonic diagnostic apparatus, and FIG. 2 is a block diagram showing the specific configurations of a transmission/reception section and a reception signal processing unit provided in the ultrasonic diagnostic apparatus. Further, FIG. 4 is a block diagram showing the configurations of a volume data generating unit and an image data generating unit provided in the ultrasonic diagnostic apparatus.

An ultrasonic diagnostic apparatus 100 shown in FIG. 1 comprises: an ultrasonic probe 3 in which a plurality of oscillating elements are arranged to transmit an ultrasonic pulse (transmission ultrasonic waves) to a three-dimensional region of a specimen and convert ultrasonic reflected waves (reception ultrasonic waves) obtained by the transmission into electric signals (reception signals); a transmission/reception section 2 which supplies the oscillating elements with a drive signal for transmitting the ultrasonic pulse in a predetermined direction of the specimen, and phases and adds the reception signals of a plurality of channels obtained from the oscillating elements; a reception signal processing unit 4 which processes the phased reception signals to generate B mode data; a volume data generating unit 5 which composes two-dimensional ultrasound data (B mode data) collected from a plurality of sequential image sections (slice sections) in the three-dimensional region to generate volume data; an image data generating unit 6 which generates three-dimensional image data on the basis of the volume data; and a display unit 7 which displays the obtained three-dimensional image data.

The ultrasonic diagnostic apparatus 100 further comprises: a gain correction data generating section 8 which generates a gain correction map for each of the plurality of sequential slice sections in the three-dimensional region on the basis of the amplitude value of the ultrasound data collected in the slice sections extracted at predetermined intervals from among the above slice sections, and then interpolates the obtained gain correction map in a slice direction to generate three-dimensional gain correction data; an input section 9 for inputting specimen information, setting image data generating conditions, etc.; a scan control unit 10 which controls the transmission/reception direction of the ultrasonic waves in a volume data collection scan mode intended for the collection of the volume data and in a gain correction scan mode intended for the collection of gain correction ultrasound data (i.e., the above-mentioned biological data and noise data); and a system control unit 11 which performs overall control of the above-mentioned respective units.

The ultrasonic probe 3 has, in the vicinity of its distal end, unshown two-dimensionally arranged M oscillating elements, and transmits and receives ultrasonic waves with this distal end in touch with the body surface of the specimen. Each of the oscillating elements incorporated in the ultrasonic probe 3 is an electroacoustic transducer element for converting an electric pulse (drive signal) into an ultrasonic pulse (transmission ultrasonic waves) at the time of transmission and converting ultrasonic reflected waves (reception ultrasonic waves) into an electric reception signal at the time of reception, and is connected to the transmission/reception section 2 via unshown multicore cables of M channels.

In addition, the ultrasonic probe 3 includes, for example, a sector scan compliant ultrasonic probe, a linear scan compliant ultrasonic probe and convex scan compliant ultrasonic probe, and an operator can select any one of them depending on a diagnostic part. While the case of using the sector scan ultrasonic probe 3 having M two-dimensionally arranged oscillating elements is described in the present embodiment, the ultrasonic probe may be the linear scan compliant ultrasonic probe or the convex scan compliant ultrasonic probe.

Next, the transmission/reception section 2 shown in FIG. 2 comprises a transmission unit 21 for supplying a drive signal to the oscillating elements of the ultrasonic probe 3, and a reception unit 22 for phasing the reception signals obtained from the oscillating elements.

The transmission unit 21 includes a rate pulse generator 211, a transmission delay circuit 212 and a drive circuit 213, and the rate pulse generator 211 generates a rate pulse for deciding the repetition period of the transmission ultrasonic waves and supplies this rate pulse to the transmission delay circuit 212. The transmission delay circuit 212 is composed of as many independent delay circuits as Mt oscillating elements used for transmission, and provides the rate pulse with a focusing delay time for focusing the transmission ultrasonic waves at a predetermined depth and with a deflection delay time for transmission in a predetermined direction ($\theta p$, $\phi q$), and then supplies the rate pulse to the drive circuit 213. The drive circuit 213 has as many independent drive circuits as those of the transmission delay circuit 212, and drives Mt ($Mt \leq M$) oscillating elements selected for transmission by the ultrasonic probe 3 from among M two-dimensionally arranged oscillating elements, thereby emitting the transmission ultrasonic waves into the body of the specimen.

On the other hand, the reception unit 22 comprises a gain setter 220, an A/D converter 221 and a reception delay circuit 222 of Mr channels corresponding to Mr ($Mr \leq M$) oscillating elements selected for reception from among M oscillating elements incorporated in the ultrasonic probe 3, and an adder 223 of one channel.

The gain setter 220 has an amplifier circuit capable of temporally changing its gain, and sets the gains of the reception signals supplied from Mr reception oscillating elements in the ultrasonic probe 3 on the basis of the gain correction data supplied from the input section 9 or the gain correction data generating section 8 via the system control unit 11. Then, the reception signals of Mr channels amplified with predetermined gains in the gain setter 220 are converted into digital signals in the A/D converter 221, and sent to the reception delay circuit 222.

The reception delay circuit 222 provides each of the reception signals of Mr channels output from the A/D converter 221 with a focusing delay time for focusing the reception ultrasonic waves from a predetermined depth and with a deflection delay time for setting reception directivity in a predetermined direction ($\theta p$, $\phi q$), and the adder 223 adds and composes together the reception signals from the reception delay circuit 222. That is, the reception signals obtained from a predetermined direction are phased and added by the reception delay circuit 222 and the adder 223.

Figure 3:
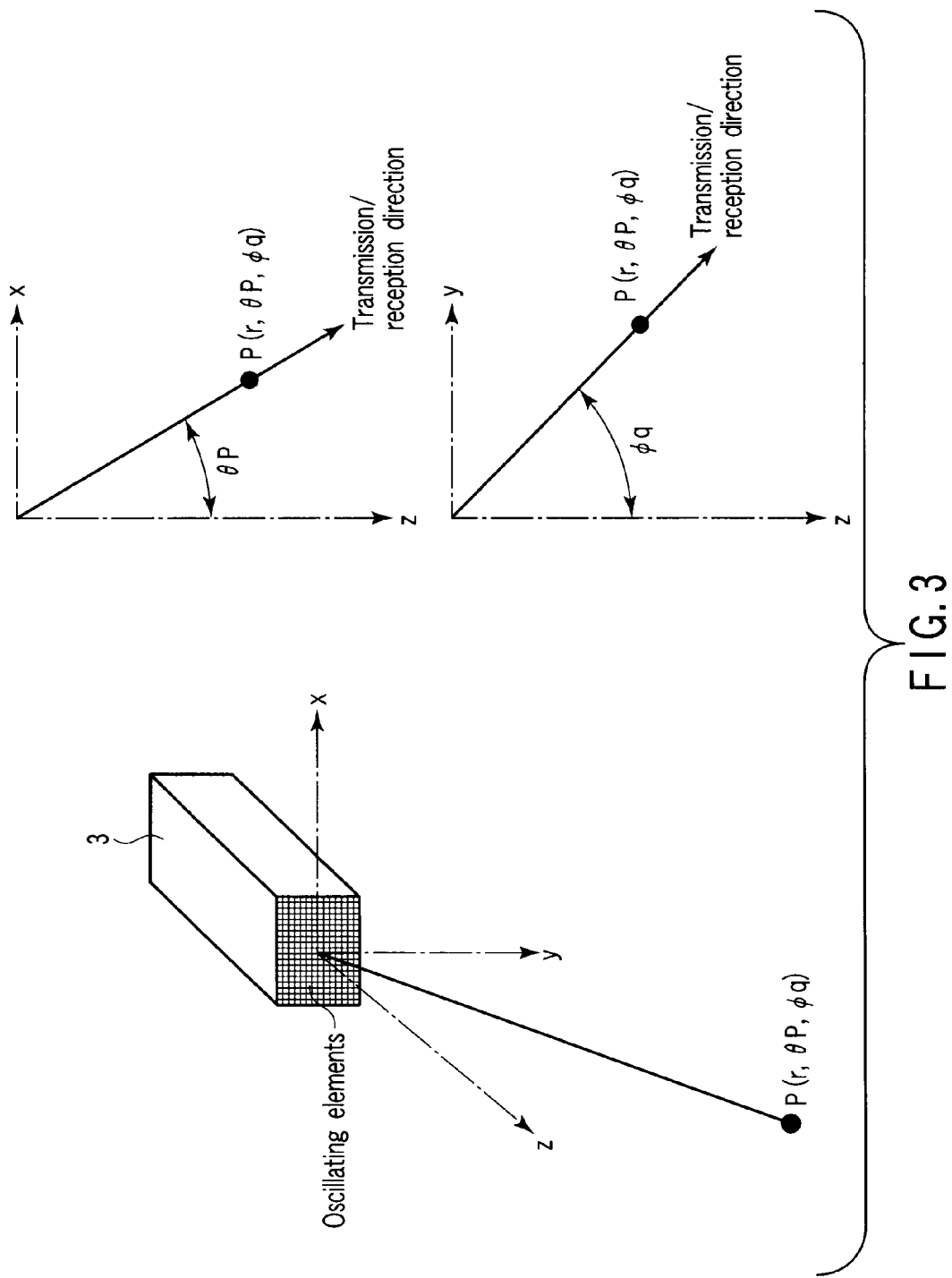
FIG. 3 is a diagram for explaining the transmission/reception direction of ultrasonic waves in a three-dimensional scan in the present embodiment.

FIG. 3 shows the transmission/reception direction ($\theta p$, $\phi q$) of ultrasonic waves in rectangular coordinates (x-y-z) in which the central axis of the ultrasonic probe 3 is defined as a z axis. In this case, the oscillating elements are two-dimensionally arranged in the x-axis direction and y-axis direction, and $\theta p$, $\phi q$ indicate angles relative to the z axis in the transmission/reception direction projected on an x-z plane and a y-z plane.

In addition, the reception delay circuit 222 and the adder 223 can have their delay times controlled to perform so-called parallel simultaneous reception for simultaneously forming reception directivities in a plurality of directions. The use of this parallel simultaneous reception method dramatically reduces the time required for the collection of the volume data.

Returning to FIG. 2, the reception signal processing unit 4 comprises an envelope detector 41 and a logarithmic converter 42. The envelope detector 41 envelope-detects the phased and added reception signals supplied from the adder 223 of the reception unit 22. The logarithmic converter 42 logarithmically converts the amplitudes of the envelope-detected reception signals to generate B mode data as ultrasound data. In addition, the envelope detector 41 and the logarithmic converter 42 may be configured in a reverse order.

Next, the specific configurations of the volume data generating unit 5 and the image data generating unit 6 shown in FIG. 1 are described with FIG. 4. The volume data generating unit 5 has a function to perform preferred gain setting and interpolating calculation on the three-dimensional ultrasound data (B mode data) supplied from the reception signal processing unit 4 to generate volume data in collecting the volume data for the specimen. As shown in FIG. 4, the volume data generating unit 5 comprises a gain setting unit 51, an ultrasound data storage unit 52, an interpolating calculation unit 53 and a volume data storage unit 54.

The gain setting unit 51 comprises an unshown multiplication circuit, and sets the gain of the ultrasound data supplied from the reception signal processing unit 4 on the basis of the gain correction data supplied from the input section 9 or the gain correction data generating section 8 via the system control unit 11. Moreover, the ultrasound data storage unit 52 stores, together with information on the transmission/reception direction ($\theta p$, $\phi q$), the ultrasound data collected by the three-dimensional scan of the diagnostic part and amplified with a predetermined gain in the gain setting unit 51.

On the other hand, the interpolating calculation unit 53 reads the three-dimensional ultrasound data temporarily stored in the ultrasound data storage unit 52 and the transmission/reception direction ($\theta p$, $\phi q$) of the ultrasonic waves as the collateral information, and performs the interpolating calculation of the ultrasound data arranged to correspond to the transmission/reception direction ($\theta p$, $\phi q$), thereby generating volume data composed of isotropic voxels. Then, the generated volume data is stored in the volume data storage unit 54.

Next, the image data generating unit 6 has a function to render the volume data generated in the volume data generating unit 5 to generate three-dimensional image data. The image data generating unit 6 comprises a histogram calculation unit 61, an opacity/tone setting unit 62 and a rendering processing unit 63.

The histogram calculation unit 61 calculates a histogram indicating the frequency of each voxel value for the voxel value of the volume data supplied from the volume data storage unit 54 of the volume data generating unit 5, and the opacity/tone setting unit 62 sets an opacity and a tone for each voxel in the volume data on the basis of the histogram. The rendering processing unit 63 renders the volume data supplied from the volume data storage unit 54 of the volume data generating unit 5 on the basis of information on the opacity and tone set by the opacity/tone setting unit 62, thereby generating three-dimensional image data.

FIG. 5 is a diagram for schematically explaining an opacity/tone Op set by the opacity/tone setting unit 62 for a histogram Hg calculated by the histogram calculation unit 61. The opacity/tone Op having, for example, S-shaped characteristics or linear characteristics is set for a pixel value range [$\alpha 1$-$\alpha 2$] of the histogram Hg containing a predetermined percent (e.g., 90%) of image value frequency.

Returning to FIG. 1, the display unit 7 comprises a display data generating circuit, a conversion circuit and a monitor that are not shown. The display data generating circuit adds collateral information such as specimen information to the three-dimensional image data generated in the rendering processing unit 63 of the image data generating unit 6 to generate display data. On the other hand, the conversion circuit subjects the display data generated by the display data generating circuit to D/A conversion and television format conversion to display the display data on the monitor.

Next, the gain correction data generating section 8 comprises a gain correction ultrasound data storage unit 81, a living tissue region determining unit 82, a gain correction map generating unit 83 and an interpolating processing unit 84.

The gain correction ultrasound data storage unit 81 includes a biological data storage region and a noise data storage region that are not shown. Then, before the collection of the volume data for the specimen, the ultrasound data in a plurality of slice sections supplied from the reception signal processing unit 4 in a gain correction scan mode intended for the generation of three-dimensional gain correction data for the volume data is stored as gain correction ultrasound data. As this gain correction ultrasound data, normal ultrasound data (biological data) collected in the slice sections with an initial gain and ultrasound data (noise data) collected without any transmission/reception of ultrasonic waves are stored in their storage regions together with slice section identification information, information on the transmission/reception direction of the ultrasonic waves, etc.

FIG. 6A and FIG. 6B show the three-dimensional ultrasound data collected in the volume data collection scan mode, and two-dimensional ultrasound data for a plurality of slice sections collected in the gain correction scan mode. The three-dimensional ultrasound data collected in the volume data collection scan mode is generated on the basis of the transmission/reception of the ultrasonic waves of $\theta p=\theta 1$ to $\theta p$ in slice sections of $\phi q=\phi 1$ to $\phi Q$ set at small intervals of $\Delta\phi$ in a $\phi q$ direction, as shown in FIG. 6A.

On the other hand, the plurality of two-dimensional ultrasound data collected in the gain correction scan mode are generated on the basis of the transmission/reception of the ultrasonic waves of $\theta p=\theta 1$ to $\theta p$ in slice sections of $\phi q=\phi 1$, $\phi 5$, $\phi 9$, . . . set at intervals of $4\Delta\phi$, for example, in a $\phi q$ direction, as shown in FIG. 6B. That is, the plurality of slice sections in the gain correction scan mode are set by extracting, at intervals of $4\Delta\phi$, a plurality of slice sections in the volume data collection scan mode arranged at intervals of $\Delta\phi$ in the $\phi p$ direction.

Next, the living tissue region determining unit 82 includes an unshown calculation circuit. The living tissue region determining unit 82 reads the two-dimensional biological data and noise data temporarily stored in the gain correction ultrasound data storage unit 81, and calculates an S/N by the difference between the two. The living tissue region determining unit 82 further divides a region having an S/N higher than a preset threshold value into predetermined sizes to set a plurality of first regions, and calculates a dispersion value for the biological data in the first regions. Then, a living tissue region in the biological data is determined on the basis of the obtained dispersion value. That is, a living tissue region having an S/N value higher than a predetermined threshold value and having a dispersion value belonging in a predetermined threshold range is extracted, which is differentiated from noise dominant regions and regions having artifact or tissue boundaries such as blood vessel walls.

Next, the gain correction map generating unit 83 bundles the adjacent first regions into predetermined sizes to form a plurality of second regions, and applies a least squares method to the average value of the biological data in each of the second regions, thereby generating a two-dimensional sensitivity map. Then, the value of the sensitivity map is subtracted from a preset reference gain value to generate a two-dimensional gain correction map.

On the other hand, the interpolating processing unit 84 has a storage circuit. The interpolating processing unit 84 interpolates, in the $\phi q$ direction, the gain correction map generated by the gain correction map generating unit 83 for each of the slice sections of $\phi q=\phi 1$, $\phi 5$, $\phi 9$, . . . , and generates, for example, three-dimensional gain correction data corresponding to each voxel of the volume data. Then, the obtained gain correction data is stored in the storage circuit.

In addition, the method of determining the living tissue region by the living tissue region determining unit 82 and the method of generating the gain correction map by the gain correction map generating unit 83 are described in Patent document 2 mentioned above and are not described in more detail.

Returning again to FIG. 1, the input section 9 comprises a scan mode selecting unit 91 for selecting the gain correction scan mode and the volume data collection scan mode using input devices such as a display panel on an operation panel, a keyboard, a track ball, a mouse, a selection button and an input button, a slice section setting unit 92 for setting the intervals and angles of the slice sections in the gain correction scan mode, a gain characteristic setting unit 93 for manually setting gain characteristics for the reception signals and the ultrasound data, and a gain setting mode selecting unit 94 for selecting an automatic setting mode or manual setting mode of the gain correction. Moreover, the above-mentioned display panel and input devices are also used for the input of the specimen information, the setting of volume data generating conditions, the setting of three-dimensional image data generating conditions and display conditions, and the input of various command signals.

Next, the scan control unit 10 sets the transmission/reception directions of the ultrasonic waves in the gain correction scan mode and the volume data collection scan mode set on the basis of the above-mentioned volume data generating conditions and information on the slice sections set by the slice section setting unit 92 of the input section 9, and also sets delay times necessary for the transmission/reception of the ultrasonic waves in these transmission/reception directions, for the transmission delay circuit 212 of the transmission unit 21 and the reception delay circuit 222 of the reception unit 22.

The system control unit 11 comprises a CPU and a storage circuit that are not shown. The storage circuit stores the above-mentioned various kinds of information input/selected/set in the input section 9. Then, the CPU performs overall control of the respective units of the ultrasonic diagnostic apparatus 100 on the basis of the above-mentioned input/selected/set information. In particular, the gain correction data automatically set in the gain correction data generating section 8 or the gain correction data based on the gain characteristics manually set in the gain characteristic setting unit 93 of the input section 9 is supplied to the gain setter 220 in the reception unit 22 of the transmission/reception section 2 to set the gains of the reception signals. Moreover, the gain correction data is supplied to the gain setting unit 51 of the volume data generating unit 5 to set the gain of the ultrasound data supplied from the reception signal processing unit 4.

(Procedure of Generating Gain Correction Data)

Figure 7:
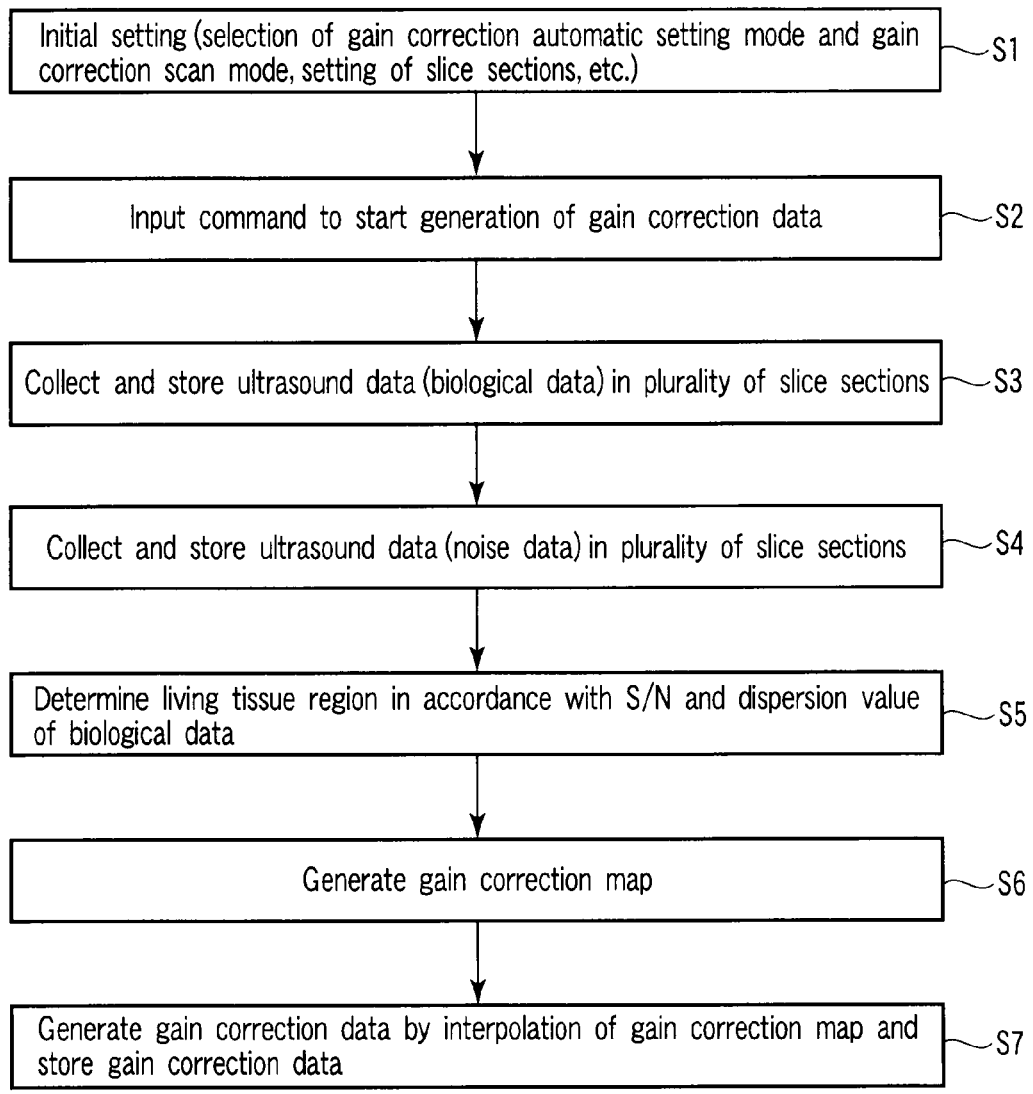
FIG. 7 is a flowchart showing a procedure of generating three-dimensional gain correction data in the present embodiment.

Next, the procedure of generating the gain correction data carried out before the generation of the volume data of the specimen is described with a flowchart of FIG. 7.

The operator of the ultrasonic diagnostic apparatus 100 inputs the specimen information in the input section 9, and then selects the gain correction automatic setting mode in the gain setting mode selecting unit 94 of the input section 9, selects the gain correction scan mode in the scan mode selecting unit 91, sets slice sections in the slice section setting unit 92, etc. The operator further sets the volume data generating conditions, the three-dimensional image data generating conditions, display conditions, etc. (step S1 in FIG. 7).

When the initial setting described above has been completed, the operator selects the collection of the B mode data in the input section 9, and inputs a command to start the generation of the gain correction data while the distal end of the ultrasonic probe 3 is being fixed at a preferred position of the body surface of the specimen (step S2 in FIG. 7). Then, this command signal is supplied to the system control unit 11, such that the collection of the ultrasound data (gain correction ultrasound data) intended for the generation of the gain correction data is started.

At the time of the collection of the gain correction ultrasound data, the rate pulse generator 211 of the transmission unit 21 shown in FIG. 2 generates a rate pulse in accordance with a control signal supplied from the system control unit 11 and supplies the rate pulse to the transmission delay circuit 212. The transmission delay circuit 212 provides the rate pulse with a delay time for transmitting the ultrasonic waves in the initial transmission/reception direction ($\theta 1$, $\phi 1$) set by the scan control unit 10 on the basis of the slice section information supplied from the slice section setting unit 92 of the input section 9 via the system control unit 11, and with a delay time for focusing the ultrasonic waves at a predetermined depth to obtain a small transmission beam width. The transmission delay circuit 212 supplies this rate pulse to the drive circuit 213 of Mt channels.

The drive circuit 213 generates a drive signal having a predetermined delay time on the basis of the rate pulse supplied from the transmission delay circuit 212, and supplies this drive signal to Mt transmission oscillating elements in the ultrasonic probe 3, so that the transmission ultrasonic waves are emitted to the specimen. Part of the emitted transmission ultrasonic waves is reflected by the interface between organs different in acoustic impedance or by tissues, and received by Mr reception oscillating elements and converted into electric reception signals of Mr channels.

This reception signal is amplified at a predetermined amplitude level in the gain setter 220 of the reception unit 22, and then converted into a digital signal in the A/D converter 221. Then, the reception delay circuit 222 of Mr channel provides the converted reception signal with a delay time for focusing the ultrasonic waves received from a predetermined depth and with a delay time for attaching strong reception directivity to the ultrasonic waves received from the initial ultrasonic wave transmission/reception direction ($\theta 1$, $\phi 1$) set by the scan control unit 10. The adder 223 phases and adds the reception signals output from the reception delay circuit 222. Then, the envelope detector 41 and the logarithmic converter 42 of the reception signal processing unit 4 to which the phased and added reception signals are supplied subject the reception signals to envelope detection and a logarithmic conversion to generate ultrasound data, and the ultrasound data is stored as biological data in the gain correction ultrasound data storage unit 81 of the gain correction data generating section 8.

When the generation and storage of the ultrasound data in the transmission/reception direction ($\theta 1$, $\phi 1$) have been completed, the transmission and reception of the ultrasonic waves are carried out in the same procedure in each of the transmission/reception directions ($\theta 2$, $\phi 1$) to ($\theta P$, $\phi 1$), and ultrasound data obtained at this point is also stored in the gain correction ultrasound data storage unit 81. That is, two-dimensional ultrasound data in the slice section of $\phi q = \phi 1$ obtained by the transmission/reception of the ultrasonic waves in the transmission/reception directions ($\theta 1$, $\phi 1$) to ($\theta P$, $\phi 1$) is stored as biological data in the gain correction ultrasound data storage unit 81.

Likewise, the scan control unit 10 transmits/receives ultrasonic waves of $\theta p = \theta 1$ to $\theta P$ in the slice sections of $\phi q = \phi 5$, $\phi 9$, $\phi 13$, ... set at intervals of $4\Delta\phi$ in a $\phi q$ direction, and two-dimensional ultrasound data obtained at this point is also stored as biological data in the gain correction ultrasound data storage unit 81 (step S3 in FIG. 7).

When the generation and storage of the biological data in the slice sections of $\phi q = \phi 1$, $\phi 5$, $\phi 9$, ... have been completed, the same gain correction scan mode is repeated with the drive circuit 213 stopped, such that the ultrasound data in the slice sections of $\phi q = \phi 1$, $\phi 5$, $\phi 9$, ... are generated, and the obtained ultrasound data are stored as noise data in the gain correction ultrasound data storage unit 81 (step S4 in FIG. 7). That is, two-dimensional biological data and noise data obtained in the slice sections of $\phi q = \phi 1$, $\phi 5$, $\phi 9$, ... are stored in the respective storage regions in the gain correction ultrasound data storage unit 81.

When the collection and storage of the biological data and noise data in the above-mentioned slice sections have been completed, the living tissue region determining unit 82 of the gain correction data generating section 8 calculates an S/N by the difference between the biological data and noise data in the slice section of $\phi q = \phi 1$ read from the gain correction ultrasound data storage unit 81. Then, a region having an S/N higher than a preset threshold value is divided into predetermined sizes to set a plurality of first regions, and the living tissue region is determined for the biological data in the slice section on the basis of the dispersion value of the biological data in the first regions (step S5 in FIG. 7).

Next, the gain correction map generating unit 83 bundles the plurality of adjacent first regions into predetermined sizes to form a plurality of second regions, and applies a least squares method to the average value of the biological data in each of the second regions, thereby generating a two-dimensional sensitivity map. Then, the value of the sensitivity map is subtracted from a preset reference gain value to generate a two-dimensional gain correction map for the slice section of $\phi q=\phi 1$ (step S6 in FIG. 7). Further, gain correction maps for the slice sections of $\phi q=5$, $\phi 9$, . . . are generated in the same procedure.

When the generation of the gain correction maps for the slice sections of $\phi q=\phi 1$, $\phi 5$, $\phi 9$, . . . has been completed, the interpolating processing unit 84 interpolates these gain correction maps in the $\phi q$ direction, and generates three-dimensional gain correction data corresponding to each voxel of the volume data collected in the volume data collection scan mode. Then, the interpolating processing unit 84 stores the obtained gain correction data in its unshown storage circuit (step S7 in FIG. 7).

(Procedure of Generating Three-dimensional Image Data)

Figure 8:
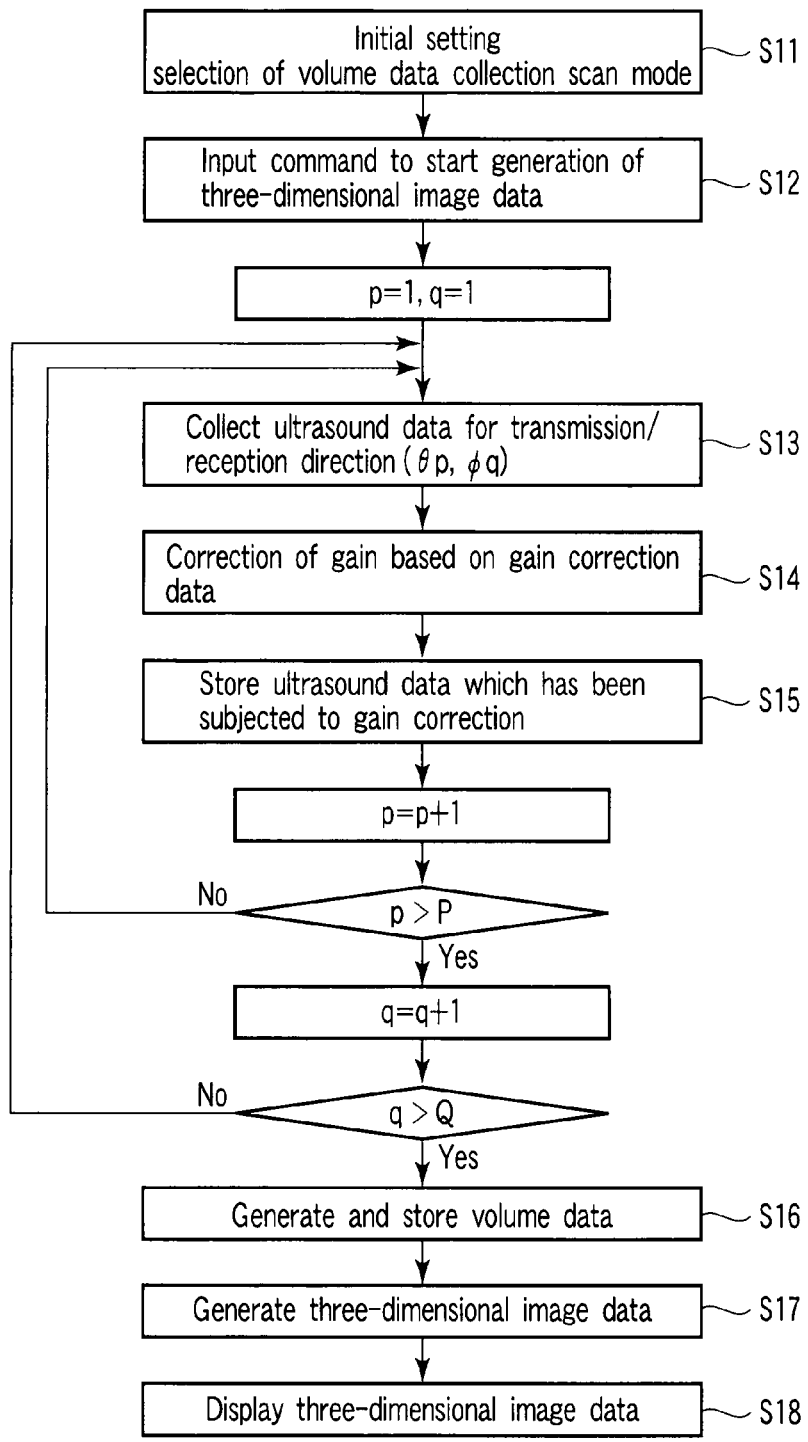
FIG. 8 is a flowchart showing a procedure of generating three-dimensional image data in the present embodiment.

Next, the procedure of generating the three-dimensional image data on the basis of the volume data which has been subjected to a gain correction (gain setting) by the above-mentioned gain correction data is described with a flowchart in FIG. 8.

When the generation and storage of the three-dimensional gain correction data for the volume data have been completed in step S7, the operator of the ultrasonic diagnostic apparatus 100 selects the volume data collection scan mode in the scan mode selecting unit 91 of the input section 9 (step S11 in FIG. 8), and inputs, from the input section 9, a command to start the generation of the three-dimensional image data while the distal end of the ultrasonic probe 3 is being fixed at the same position. Then, this command signal is supplied to the system control unit 11, such that the generation of the volume data for the specimen is started (step S12 in FIG. 8).

At the time of the generation of the volume data, the system control unit 11 and the scan control unit 10 control the transmission unit 21 and the reception unit 22 of the transmission/reception section 2 and the reception signal processing unit 4 in the same procedure as described above to transmit and receive ultrasonic waves in the transmission/reception direction ($\theta 1$, $\phi 1$), and process the reception signals obtained at this point to generate ultrasound data (B mode data) (step S13 in FIG. 8). At this moment, the gain setter 220 of the reception unit 22 makes a gain correction to the reception signals supplied from the ultrasonic probe 3 on the basis of the gain correction data corresponding to the transmission/reception direction ($\theta 1$, $\phi 1$) supplied from the interpolating processing unit 84 of the gain correction data generating section 8 via the system control unit 11.

Furthermore, the gain setting unit 51 of the volume data generating unit 5 makes a gain correction to the ultrasound data in the transmission/reception direction ($\theta 1$, $\phi 1$) supplied from the reception signal processing unit 4 on the basis of the gain correction data corresponding to the transmission/reception direction ($\theta 1$, $\phi 1$) supplied from the interpolating processing unit 84 of the gain correction data generating section 8 via the system control unit 11 (step S14 in FIG. 8). Then, the ultrasound data which has been subjected to the gain correction is stored in the ultrasound data storage unit 52 together with information on the transmission/reception direction ($\theta 1$, $\phi 1$) as collateral information (step S15 in FIG. 8).

Likewise, ultrasound data are generated for the transmission/reception direction ($\theta p$, $\phi 1$) ($\theta p=\theta 2$ to $\theta P$) and the ultrasound data are subjected to a gain correction and stored. Further, ultrasound data are generated for the transmission/reception direction ($\theta p$, $\phi q$) ($\theta p=\theta 1$ to $\theta P$, $\phi q=\phi 2$ to $\phi Q$) and the ultrasound data are subjected to a gain correction and stored. That is, three-dimensional ultrasound data which have been generated in the sequential slice sections of $\phi 1=\phi Q$ and subjected to the gain correction in the gain setting unit 51 are stored in the ultrasound data storage unit 52 together with information on the transmission/reception direction ($\theta p$, $\phi q$) ($\theta p=\theta 1$ to $\theta P$, $\phi q=\phi 1$ to $\phi Q$) (steps S13 to S15 in FIG. 8).

Next, the interpolating calculation unit 53 of the volume data generating unit 5 reads the three-dimensional ultrasound data temporarily stored in the ultrasound data storage unit 52 as well as the transmission/reception direction ($\theta p$, $\phi q$) of the ultrasonic waves as collateral information, and performs the interpolating calculation of the ultrasound data three-dimensionally arranged to correspond to the transmission/reception direction ($\theta p$, $\phi q$), thereby generating volume data composed of isotropic voxels. Then, the generated volume data is stored in the volume data storage unit 54 (step S16 in FIG. 8).

On the other hand, the histogram calculation unit 61 of the image data generating unit 6 calculates, as a histogram, the frequency of each voxel value in the volume data supplied from the volume data storage unit 54 of the volume data generating unit 5, and the opacity/tone setting unit 62 sets an opacity and a tone for each voxel in the volume data on the basis of the histogram. The rendering processing unit 63 then renders the volume data supplied from the volume data storage unit 54 on the basis of information on the opacity and tone set by the opacity/tone setting unit 62, thereby generating three-dimensional image data (step S17 in FIG. 8).

Next, the display data generating circuit of the display unit 7 adds collateral information such as the specimen information to the three-dimensional image data generated in the rendering processing unit 63 of the image data generating unit 6 to generate display data. The conversion circuit subjects the display data to D/A conversion and television format conversion to display the display data on the monitor (step S18 in FIG. 8).

Then, the operations from steps S13 to S18 are repeated until the gain correction scan mode is newly selected in the scan mode selecting unit 91 of the input section 9, and the three-dimensional image data generated by the image data generating unit 6 is displayed in real time on the monitor of the display unit 7.

According to the embodiment of the present invention described above, the gain correction map of each slice section is generated on the basis of the ultrasound data collected in each of the slice sections at predetermined intervals set in the three-dimensional region of the specimen, and these gain correction maps are interpolated in the slice direction to generate three-dimensional gain correction data, so that the time required for the generation of the gain correction data can be shorter than in the case of generating the gain correction data on the basis of the ultrasound data obtained by three-dimensionally scanning the three-dimensional region. Thus, the time required for the gain correction of the volume data is reduced, and it is possible to improve time resolution in displaying the three-dimensional image data generated on the basis of the volume data which has been subjected to the gain correction.

In particular, in the case of a so-called trigger volume mode in which volume data having a predetermined time phase are collected from an organ moving hard such as a heart in accordance with a heartbeat synchronization method based on an ECG signal, it is possible to correct the gain of the volume data with accuracy and in a short time according to the method of the present embodiment.

On the other hand, as the gain correction ultrasound data in the present embodiment are collected in a relatively few slice sections of the three-dimensional region, it is not necessary for the storage circuit for storing the gain correction ultrasound data to have a high storage capacity.

While the embodiment of the present invention has been described above, the present invention is not limited to the embodiment described above, and modifications can be made. For example, in the case of the embodiment described above, ultrasonic waves are transmitted and received in each of the slice sections set at predetermined intervals in the φq direction as shown in FIG. 6B, and a plurality of gain correction maps for the slice sections obtained at this point are interpolated in the slice direction to generate the three-dimensional gain correction data. However, for example, a plurality of slice sections may be set at a predetermined angle Δη in a η direction around the central axis of the ultrasonic probe 3 as shown in FIG. 9B, and a plurality of gain correction maps obtained for these slice sections may be interpolated in the η direction to generate the three-dimensional gain correction data. According to this method, it is possible to generate gain correction data with constantly uniform accuracy independent of the x direction and y direction in FIG. 3 or the φp direction and the φq direction in FIG. 6A and FIG. 6B.

Furthermore, while the gains of the reception signals supplied from the ultrasonic probe 3 and the gain of the ultrasound data supplied from the reception signal processing unit 4 are corrected using the gain correction data generated in the gain correction data generating section 8 in the case of the embodiment described above, the gain of one of the above may be corrected. Moreover, the volume data generated in the volume data generating unit 5 and the image data generated in the image data generating unit 6 may be subjected to gain corrections using the gain correction data.

Still further, the gains of the reception signals and the ultrasound data are corrected using the gain correction data generated in the gain correction data generating section 8 in the case of the embodiment described above, but the correction of a dynamic range may be carried out in the same procedure. Moreover, the above-mentioned gain correction map in the gain correction data generating section 8 is generated by the application of the method of Patent document 2 in the case described above, but the method of Patent document 1 may be applied.

On the other hand, the gain correction data is generated using the ultrasound data collected by the ultrasonic probe 3 having two-dimensionally arranged oscillating elements in the case of the embodiment described above, but the gain correction data may be generated using ultrasound data obtained by mechanically moving or turning an ultrasonic probe having a plurality of one-dimensionally arranged oscillating elements. Likewise, the gain correction is made to the volume data collected by the ultrasonic probe 3 having two-dimensionally arranged oscillating elements in the case described above, but the gain correction may be made to the volume data obtained by mechanically moving or turning an ultrasonic probe having a plurality of one-dimensionally arranged oscillating elements. Moreover, the ultrasonic scanning method is not limited to the above-mentioned sector scan, and it may be, for example, a convex scan, a linear scan or a radial scan.

Further yet, the volume data is generated on the basis of the B mode data obtained by the transmission/reception of the ultrasonic waves to/from the three-dimensional region in the case described above, but the volume data may be generated on the basis of other ultrasound data such as color Doppler data. Moreover, the image data generating unit 6 renders the volume data to generate volume data rendering image data or surface rendering image data as three-dimensional image data in the case described above, but the volume data may be used to generate, for example, maximum intensity projection (MIP) image data or multi planar reconstruction (MPR) image data.

It is to be noted that the present invention is not totally limited to the embodiment described above, and modifications of components can be made and embodied at the stage of carrying out the invention without departing from the spirit thereof. Moreover, suitable combinations of a plurality of components disclosed in the embodiment described above permit various inventions to be formed. For example, some of all the components shown in the embodiment described above may be eliminated. Further, the components in different embodiments may be suitably combined together.

What is claimed is:

1. An ultrasonic diagnostic apparatus which generates volume data on the basis of ultrasound data collected by transmitting/receiving ultrasonic waves to/from a three-dimensional region of a specimen, and displays, in real time, image data obtained by processing the volume data, the apparatus comprising:
   a scan unit which scans the three-dimensional region by transmitting ultrasonic waves to the three-dimensional region and receiving ultrasonic waves from the three-dimensional region;
   a control unit which controls the scan unit so as to perform a first scanning of a first arrangement for a number of slices and a second scanning, the second scanning being performed with a first arrangement for a number of slices higher than the first scanning;
   a gain correction data generating unit which generates three-dimensional gain correction data for the volume data on the basis of the received ultrasonic waves in the first scanning; and
   a gain setting unit which sets, on the basis of the gain correction data, a gain of at least one of signals based on the received ultrasonic waves obtained by the second scanning.

2. The ultrasonic diagnostic apparatus according to claim 1, comprising: a slice section setting unit which sets a plurality of slice sections in the three-dimensional region; and a scan control unit which controls the transmission/reception of the ultrasonic waves in the slice sections,
   wherein the gain correction data generating unit interpolates a plurality of gain correction maps based on the ultrasound data collected in the respective slice sections to generate the gain correction data.

3. The ultrasonic diagnostic apparatus according to claim 2, wherein the slice section setting unit sets the plurality of slice sections into a slice direction in the three-dimensional ultrasound data collected for the purpose of generating the volume data, the plurality of slice sections having an arrangement interval wider than an interval in the slice direction.

4. The ultrasonic diagnostic apparatus according to claim 2, wherein the slice section setting unit sets the plurality of slice sections at predetermined angles and intervals around the central axis of the transmission/reception of the ultrasonic waves to/from the three-dimensional region of the specimen.

5. The ultrasonic diagnostic apparatus according to claim 2, wherein the gain correction data generating unit includes:
   a living tissue region determining unit which determines a living tissue region in the slice section on the basis of an S/N and a dispersion value of the ultrasound data;
   a gain correction map generating unit which generates a two-dimensional gain correction map on the basis of the ultrasound data in the living tissue region determined by the living tissue region determining unit; and an interpolating processing unit which interpolates the plurality of gain correction maps obtained from the respective slice sections to generate the gain correction data.

6. The ultrasonic diagnostic apparatus according to claim 2, wherein the gain correction data generating unit interpolates the gain correction map obtained from each of the slice sections of the first scanning to generate the gain correction data corresponding to each voxel of the volume data.

7. The ultrasonic diagnostic apparatus of claim 6, wherein the interpolation for the gain map is a spatial interpolation, in which data points of the gain map corresponding to the first scanning are interpolated to the data points corresponding to the second scanning.

8. The ultrasonic diagnostic apparatus according to claim 1, further comprising: an image data generating unit which generates any one of volume rendering image data, surface rendering image data, MIP image data and MPR image data on the basis of the volume data whose gain has been set by the gain correction data.

9. The ultrasonic diagnostic apparatus according to claim 1, wherein the gain setting unit sets a gain and a dynamic range for at least one of the reception signal and the ultrasound data on the basis of the gain correction data.

10. A method of controlling an ultrasonic diagnostic apparatus which generates volume data on the basis of ultrasound data collected by transmitting/receiving ultrasonic waves to/from a three-dimensional region of a specimen, and displays, in real time, image data obtained by processing the volume data, the method comprising:
providing a scan unit to scan the three-dimensional region by transmitting ultrasonic waves to the three-dimensional region and receiving ultrasonic waves from the three-dimensional region;
controlling the scan unit so as to perform a first scanning of a first arrangement for a number of slices and a second scanning, the second scanning being performed with a first arrangement for a number of slices higher than the first scanning;
generating three-dimensional gain correction data for the volume data on the basis of the received ultrasonic waves in the first scanning; and
setting, on the basis of the gain correction data, a gain of at least one of signals based on the received ultrasonic waves obtained by the second scanning.

11. The ultrasonic diagnostic apparatus control method according to claim 10, comprising:
setting a plurality of slice sections in the three-dimensional region; and controlling the transmission/reception of the ultrasonic waves in the slice sections,
wherein in the generation of the gain correction data, a plurality of gain correction maps based on the ultrasound data collected in the respective slice sections are interpolated to generate the gain correction data.

12. The ultrasonic diagnostic apparatus control method according to claim 11, wherein in the setting of the slice sections, the plurality of slice sections are set into a slice direction in the three-dimensional ultrasound data collected for the purpose of generating the volume data, the plurality of slice sections having an arrangement interval wider than an interval in the slice direction.

13. The ultrasonic diagnostic apparatus control method according to claim 11, wherein in the setting of the slice sections, the plurality of slice sections are set at predetermined angles and intervals around the central axis of the transmission/reception of the ultrasonic waves to/from the three-dimensional region of the specimen.

14. The ultrasonic diagnostic apparatus control method according to claim 11, wherein in the generation of the gain correction data,
a living tissue region in the slice section is determined on the basis of an S/N and a dispersion value of the ultrasound data,
a two-dimensional gain correction map is generated on the basis of the ultrasound data in the determined living tissue region, and
the plurality of gain correction maps obtained from the respective slice sections are interpolated to generate the gain correction data.

15. The ultrasonic diagnostic apparatus control method according to claim 11, wherein in the generation of the gain correction data, the gain correction map obtained from each of the slice sections is interpolated to generate the gain correction data corresponding to each voxel of the volume data.

16. The ultrasonic diagnostic apparatus control method according to claim 10, further comprising: generating any one of volume rendering image data, surface rendering image data, MIP image data and MPR image data on the basis of the volume data whose gain has been set by the gain correction data.

17. The ultrasonic diagnostic apparatus control method according to claim 10, wherein in the setting of the gain, a gain and a dynamic range are set for at least one of the reception signal and the ultrasound data on the basis of the gain correction data.

* * * * *